United States Patent [19]

Feder et al.

[11] 4,301,312

[45] Nov. 17, 1981

[54] METHOD AND SYSTEM FOR ETHANOL PRODUCTION

[75] Inventors: Harold M. Feder; Michael J. Chen, both of Darien, Ill.

[73] Assignee: The United States of America as represented by the United States Department of Energy, Washington, D.C.

[21] Appl. No.: 151,996

[22] Filed: May 21, 1980

[51] Int. Cl.³ .................. C07C 27/00; C07C 29/32; C07C 29/36

[52] U.S. Cl. .................. 568/902; 252/428

[58] Field of Search .......................... 568/902

[56] References Cited

U.S. PATENT DOCUMENTS

| | | | |
|---|---|---|---|
| 3,297,768 | 1/1967 | Kindler et al. | 568/909 |
| 3,631,111 | 12/1971 | Tucci | 568/909 |
| 4,152,248 | 5/1979 | Feder et al. | 208/144 |
| 4,201,868 | 5/1980 | Slinkard | 568/902 |

FOREIGN PATENT DOCUMENTS 1937 5/1979 European Pat. Off. ............. 568/902

OTHER PUBLICATIONS

C&EN, Apr. 7, 1980, "Methanol Carbonylation Selectivity Improved", pp. 37-38.
Walker et al., "J.A.C.S.", 101:24, Nov. 21, 1979, pp. 7428-7429.
Wender et al., "Science", vol. 113, (1951), pp. 206-207.
Wada et al., "JOMC" 61, pp. 365-373, 1973.
Chem. Econ. Eng. Rev. 11 (5) 15 (1979), Ethanol from Synthesis Gas.
Ichikawa, "J.C.S. Chem. Comm.", 1978, pp. 566-567.
Koermer et al., Ind. Eng. Chem. Prod. Res. Dev., vol. 17, No. 3, 1978, pp. 231-236.

Primary Examiner—Joseph E. Evans
Attorney, Agent, or Firm—Hugh W. Glenn; Robert J. Fisher; Richard G. Besha

[57] ABSTRACT

A transition metal carbonyl and a tertiary amine are employed as a homogeneous catalytic system in methanol or a less volatile solvent to react methanol with carbon monoxide and hydrogen gas producing ethanol and carbon dioxide. The gas contains a high carbon monoxide to hydrogen ratio as is present in a typical gasifier product. The reaction has potential for anhydrous ethanol production as carbon dioxide rather than water is produced. The only other significant by-product is methane. Selected transition metal carbonyls include those of iron, ruthenium and possibly manganese and osmium. Selected amines include trimethylamine, N-Methylpyrrolidine, 24-diazabicyclooctane, dimethyneopentylamine and 2-pryidinol.

21 Claims, 1 Drawing Figure

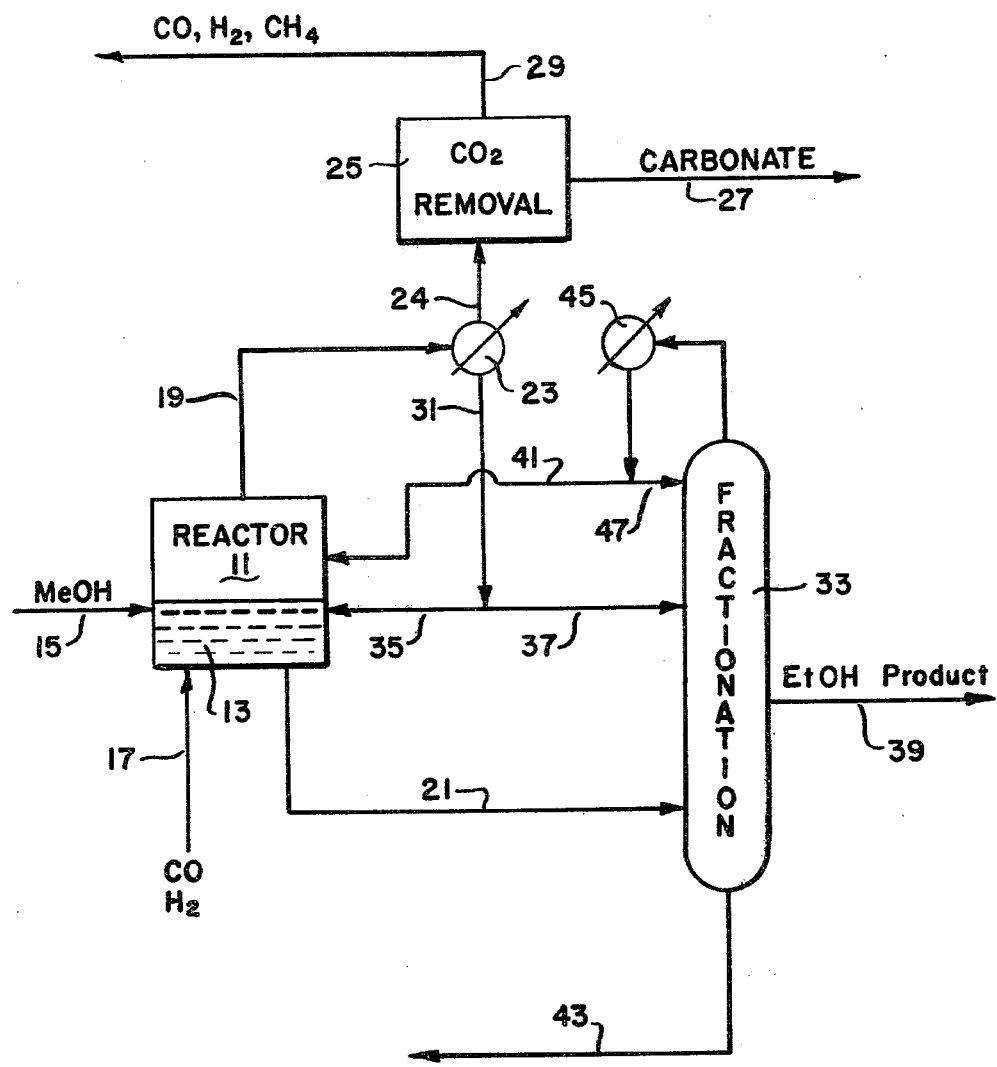

METHOD AND SYSTEM FOR ETHANOL PRODUCTION

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The present invention relates to a method and to a system for the production of ethanol. It is particularly applicable to the conversion of methanol to ethanol but also relates to the production of ethanol from gases including carbon monoxide and hydrogen. Such gases are produced in the gasification of coal or other carbonaceous material. Where carbon monoxide and hydrogen along with various gasifier products are provided as raw materials, methanol or a methanol derivative such as methyl formate is contemplated as a reactant or as in intermediate within the process and system of the present invention. Therefore the present process and system in most instances will be described in terms of the conversion of methanol to ethanol.

The catalytic system employed is a homogeneous system with a transition metal carbonyl in organic liquid solution. One previous system of this type employed dicobalt octacarbonyl as catalyst in organic solvent for the reaction of methanol with carbon monoxide and hydrogen gas. Both ethanol and water were produced along with a large variety of by products including various ethers, esters and higher alcohols as well as other by products. Attempts to improve the selectivity or activity of the cobalt catalysts by the addition of various ligands or co-catalysts were reported. Ligands such as phosphines, amines, nitriles, pyridines and phenols with co-catalysts including carbonyls of iron, chromium, manganese, rhenium, rhodium, platinum, copper and vanadium have been tested.

In other prior systems, rhodium carbonyl clusters were deposited on various metal oxides such as silica gel and alumina to act as a heterogeneous catalyst for the reaction of carbon monoxide and hydrogen gas to form products such as ethanol, methanol, acetaldehyde and acetate.

The following patents and other publications are illustrative of the general field of the present development.

U.S. Pat. No. 4,133,966, Jan. 9, 1979, discloses a process for reacting methanol with hydrogen and carbon monoxide to produce ethanol and water in the presence of cobalt acetylacetonate, a tertiary organo group V compound and a ruthenium compound.

U.S. Pat. No. 4,152,248 to Feder and Ratkhe, May 1, 1979, discloses the use of dicobalt octacarbonyl and other transition metal carbonyl catalysts in organic solvent for the hydrogenation of a coal liquid.

Wada and Matsuda, JOMC 61, 365-373, 1973 discloses the formation of mononuclear hydride anion, $HFe(CO)_4^-$ in the reaction of $Fe(CO)_5$ with water or hydrogen in the presence of tertiary amine under carbon monoxide pressure and presents insight into the behavior of iron carbonyl species under conditions comparable to those used in the hydroxymethylnation of olefins.

CHEM. ECON. ENG. REV. 11 (5) 15 (1979) "Ethanol from Synthetic Gas" and J.C.S. CHEM. COMM. 1978 "Catalytic Synthesis of Ethanol from CO and $H_2$ Under Atmospheric Pressure Over Pyrolysed Rhodium Carbonyl Clusters on $TiO_2$, $ZrO_2$ and $La_2O_3$" 566-567 disclose the production of ethanol from CO and $H_2$ gases over pyrolysed Rh carbonyl clusters dispersed on metal oxides.

IND. ENG. CHEM. PROD. RES. DEV. Vol 17, No. 3, 1978 Page 231-236 discloses the conversion of methanol to ethanol in organic solution with a cobalt carbonyl catalyst. Water and various other organic compounds are also produced.

C&EN 7, Apr. 7, 1980 "Methanol Carbonylation Selectivity Improved" 37-38 discloses the conversion of methanol to ethanol over transition metal carbonyl catalysts to produce ethanol and water.

GER. OFFEN. No. 2,625,627 discloses the reaction of methanol with carbon monoxide and hydrogen in the presence of $CoI_2$ or $CoBr_2$ a tertiary phosphine and a hydrocarbon to produce ethanol and water.

Ital. Pat. No. 484,182, Aug. 29, 1953 presents production of linear primary alcohol mixtures by the reaction of methanol, carbon monoxide and hydrogen in the presence of a catalyst material containing melted iron.

For convenience in describing the present invention the following abbreviations or symbols will be used:

Me—Methyl group, $CH_3$—
Et—Ethyl group, $C_2H_5$—
$NR_3$—Any tertiary amine with all three positions of the amine nitrogen substituted. Two of the substitutions may be to the same group as in a heterocyclic ring or by a double bond.
TM—Transition metal.
pKa—The negative logarithm of the acid dissociation constant for the acid, HB in water where $B^-$ is the conjugate base, i.e.

$$pKa = -\text{Log}\left(\frac{[H_3O^+][B^-]}{[HB]}\right)$$

Since the catalytic system of this application is in organic solution rather than water, pKa is used as an estimate of relative acidity or basicity.

pH—For purposes of this application, pH refers to actual measurements in organic solutions with commercially available pH meters rather than to the negative logarithm of the hydronium ion concentration which may not be present in the solution.

SUMMARY OF THE INVENTION

Therefore in view of the above it is an object of the present invention to provide a method of converting methanol or a methanol derivative to ethanol with minimal production of water and other by-products.

It is a further object to provide such a method in which methanol may be reacted with a gas containing hydrogen and carbon monoxide with a greater partial pressure of carbon monoxide than of hydrogen.

It is also an object to provide a method that employs a gasifier product with typically low $H_2$:CO ratio to produce ethanol from methanol.

It is another object to provide a catalytic system for producing ethanol from methanol or a methanol derivative that is characterized by a high selectivity towards ethanol.

It is yet another object to provide a catalytic system for producing ethanol from methanol in which the production of water is minimized.

In accordance with the present invention a method and catalytic system is provided for preparing ethanol by reaction of methanol or a methanol derivative such as methyl formate with a gas containing hydrogen and carbon monoxide. A solvent including methanol is used to form a solution containing the homogeneous catalytic system. The system includes in organic liquid solution, a tertiary amine and a selected transition metal carbonyl into which the $H_2$, CO gas flow is passed in intimate contact to react with methanol and form ethanol and carbon dioxide. Ethanol is separated from the solution and recovered as product. The transition metal carbonyl and tertiary amine are selected to provide protonated forms that are characterized by sufficiently close acid dissociations to permit both the protonated and the conjugate base forms of the tertiary amine and transition metal carbonyl to exist in measurable and reactable equilibrium within the catalytic system.

In a more specific aspect of the invention the transition metal carbonyls are selected from the group consisting of iron carbonyls, ruthenium carbonyls and mixtures thereof and the tertiary amines are selected from trimethylamine, N-methylpyrrolidine, 1,4-diazabicyclooctane, dimethylneopentylamine, 2-pyridinol and mixtures thereof. The process is preferably performed with less than four weight percent water in solution at measured pH levels of 9 to 13, a temperature of 180° to 220° C., and pressures of 100 to 400 atmospheres.

BRIEF DESCRIPTION OF THE DRAWING

The FIGURE is a diagrammatic flow diagram illustrating a process for converting methanol to ethanol.

DETAILED DESCRIPTION OF THE PREFERRED EMBODIMENT

The catalytic system of the present invention is that of a homogeneous catalyst dissolved in a suitable organic solvent into which the reactants methanol, carbon monoxide and hydrogen are also dissolved or included for reaction in accordance with the following overall stoichiometry.

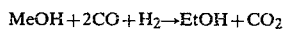

$$MeOH + 2CO + H_2 \rightarrow EtOH + CO_2$$

The catalytic system includes in solution the combination of a selected tertiary amine and a selected transition metal carbonyl that appropriately interract to provide the catalytic species needed to bring about the above overall reaction. It is to be emphasized that this reaction occurs substantially to the exclusion of water production and can advantageously use gaseous reactants having substantial excess of carbon monoxide over hydrogen. Gas mixtures with high carbon monoxide to hydrogen ratios are typically found in the gaseous products of processes for the gasification of coal and other carbonaceous materials.

The homogeneous catalytic system and the reaction not only does not produce water but is advantageously operated and provided with reactants and constitutents having minimal water content. Solvents and reaction mixtures are preferably included with less than 4 weight percent water for the effective production of ethanol.

Although the catalytic system in which the reaction occurs is contemplated as a homogeneous system, a plurality of liquid phases including co-solvents, tertiary amines transition metal carbonyls that are beyond their solubility in the principal solvent also may be provided for maintaining ample concentrations of the various constitutents in the principal reaction solution.

An important aspect of the catalytic system and process is the appropriate selection of the transition metal carbonyl such that it cooperates in solution with the tertiary amine to provide the necessary catalytic species and intermediates for carrying out the production of ethanol to the exclusion of the production of water. In making this selection, the transition metal carbonyl should provide a protonated species that dissociates by acid dissociation to a conjugate base having nucleophilic base characteristics. This acid dissociation of the protonated species should be within the range of acidity or basicity of that of the protonated cation of the selected tertiary amine. Stated differently the protonated transition metal carbonyl should have an acid dissociation constant within the general range of the acid dissociation constant of the protonated tertiary amine. These conditions provide simultaneously reactable quantities of the tertiary amine, the protonated transition metal carbonyl and of the conjugate transition metal carbonyl base in solution. Accordingly, the catalytic system should include the following equilibrium with reactable quantities of each reactant and each product.

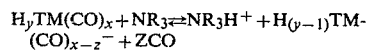

$$H_yTM(CO)_x + NR_3 \rightleftharpoons NR_3H^+ + H_{(y-1)}TM(CO)_{x-z}^- + ZCO$$

Although reactable quantities may vary from system to system including various reactants and catalytic constituents, it may be stated that each of the above reactants and products are advantageously maintained in solution by appropriate selection in a concentration of at least $10^{-5}$ moles per liter.

Since most tertiary amines considered for the catalytic system are basic having pKa's within the range of 8 to 12, protonated transition metal carbonyl species with acid dissociation constants within and somewhat above this same range are contemplated. Therefore, organic catalytic solutions with these selected combinations of catalysts typically will have pH measurements within the range of 9 to 13. However, it is to be remembered that pH as given in the present application is merely that of a measurement within an organic solution in which the hydronium ion may be absent or present only in trace quantities less than that represented by the pH measurement.

Although a number of transition metal species that meet the above requirements may be available, the inventors have identified transition metal carbonyls of iron and of ruthenium as suitable selections. Iron carbonyls may be provided in the mono-, di- or tri-nuclear forms. That is, as $Fe(CO)_5$, $Fe_2(CO)_9$ or $Fe_3(CO)_{12}$ as long as an appropriate protonated iron carbonyl species exists with suitable acid disassociation to match that of the selected tertiary amine. The protonated species contemplated are $HFe(CO)_4^-$, $HFe_2(CO)_8^-$ and $HFe_3(CO)_{11}^-$. In conjunction with the mononuclear species, it is believed that the following equilibria occurs in the catalytic reaction solution. Although the following equilibria are offered by way of explanation, the inventors do not wish to be limited to these equilibria and reactions as the complete or exclusive paths by which the present catalytic system and method operate.

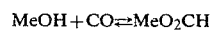

$$MeOH + CO \rightleftharpoons MeO_2CH \quad (1)$$

$$\text{MeO}_2\text{CH} + \text{NR}_3 \rightleftharpoons (\text{NR}_3\text{Me}^+, \text{O}_2\text{CH}^-) \quad (2)$$

$$\text{NR}_3 + \text{H}_2 + \text{Fe(CO)}_5 \rightleftharpoons \text{NR}_3\text{H}^+ + \text{HFe(CO)}_4^- + \text{CO} \quad (3)$$

$$\text{HFe(CO)}_4^- + \text{NR}_3 \rightleftharpoons \text{NR}_3\text{H}^+ + \text{Fe(CO)}_4^{2-} \quad (4)$$

From these equilibria the following reactions are believed to occur for the production of ethanol in solution.

$$\text{MeO}_2\text{CH} + \text{Fe(CO)}_4^{2-} \rightarrow \text{MeFe(CO)}_4^- + \text{O}_2\text{CH}^- \quad (5)$$

$$\text{NR}_3\text{Me}^+ + \text{Fe(CO)}_4^{2-} \rightarrow \text{MeFe(CO)}_4^- + \text{NR}_3 \quad (6)$$

$$\text{MeFe(CO)}_4^- + \text{CO} \rightarrow (\text{MeCO})\text{Fe(CO)}_4^- \quad (7)$$

$$\text{HFe(CO)}_4^- + \text{CO} + (\text{MeCO})\text{Fe(CO)}_4^- \rightarrow \text{MeCHO} + \text{Fe(CO)}_4^{2-} + \text{Fe(CO)}_5 \quad (8)$$

$$\text{O}_2\text{CH}^- + \text{HFe(CO)}_4^- \rightarrow \text{H}_2 + \text{CO}_2 + \text{Fe(CO)}_4^{2-} \quad (9)$$

$$2\text{HFe(CO)}_4^- + \text{CO} + \text{MeCHO} \rightarrow \text{EtOH} + \text{Fe(CO)}_4^{2-} + \text{Fe(CO)}_5 \quad (10)$$

In the above described equilibria, the reactants methanol and carbon monoxide produce methyl formate which reacts with the tertiary amine to form a methylated quaternary ammonium cation and the formate anion. From these reactions it is clear that methyl formate can be included as an initial reactant. Iron pentacarbonyl interacts with the tertiary amine and hydrogen to produce the protonated tertiary amine cation and the protonated iron carbonyl species. The interaction of this protonated iron carbonyl species and the tertiary amine in the equilbrium of equation 4 produces the strong nucleophilic iron carbonyl base, $\text{Fe(CO)}_4^{2-}$. It is this equilibrium in equation 4 that requires the protonated transition metal carbonyl species to have an acid dissociation comparable to that of the protonated tertiary amine. As will be seen, the tertiary amine, the protonated iron carbonyl species and the nucleophilic iron carbonyl base are instrumental in at least one of the reactions in the series believed to provide ethanol. It is therefore of importance that the equilibrium be driven to neither side of the equation 4 to such an extent that the molar concentration of any species be less than a reactable quantity that is less than about $10^{-5}$ moles per liter. This is accomplished by selecting tertiary amines and protonated transition metal carbonyls that have pKa's within about 5 units of the other. As an example, protonated trimethylamine and protonated iron tetracarbonyl anion have respective pKa's of about 9–10 and about 12–14.

In the above reactions (5–6) the strong nucleophilic iron tetracarbonyl dianion attacks the methyl group of methyl formate or the methyl group of the methylated quaternary ammonium cation to provide methanated iron tetracarbonyl anion. It is also possible that the protonated iron tetracarbonyl anion serves as a nucleophilic base to form a methanated iron tetracarbonyl species in a similar manner. This methanated iron tetracarbonyl species is believed to undergo an insertion reaction with carbon monoxide to form the acetyl iron tetracarbonyl anion as shown in equation 7. The protonated iron tetracarbonyl anion is instrumental as a hydrogen donor for the formation of acetaldehyde and its further hydrogenation to ethanol shown in equations 8 and 10. In equation 9 the protonated iron carbonyl donates hydrogen to convert formate anion to $\text{H}_2$ and $\text{CO}_2$ gas.

As is seen above and as will be shown in the examples given below, this proposed catalytic reaction system operates substantially without the production of water. The principal side reaction that has been observed in the above system is one which produces methane, for instance, by the hydrogenation of the methanated iron tetracarbonyl anion.

One other transition metal carbonyl system that has been found compatible with various selected tertiary amines are the carbonyls of ruthenium. In particular, triruthenium, dodecacarbonyl, $\text{Ru}_3(\text{CO})_{12}$ forms in solution the protonated species $\text{HRu}_3(\text{CO})_{11}^-$ and possibly the nucleophilic anion base $\text{Ru}_3(\text{CO})_{11}^{-2}$. Applicants believe that corresponding or similar equilibria and reactions to that in the iron system occur but do not wish to be held to these exact equilibria or reaction paths for the production of ethanol.

Various other transition metal carbonyls and homogeneous catalytic solutions may also provide the appropriate species for the conversion of methanol to ethanol. Since both iron and ruthenium carbonyls are seen to have appropriate protonated and nucleophilic species for use in combination with tertiary amines, it is reasonable to assume that carbonyls of other transition metals such as osmium or manganese also may include appropriate species. Various transition metal carbonyl hydrides that may provide species of suitable acidity or basicity to cooperate with selected tertiary amines in solution in accordance with the present process and system are given below in Table I. The data in this table is based on methanol solutions at 25° C. and is taken from Walker et al., J. of Am. Chem. Soc. (101:24), 7428 (1979).

TABLE I

| COMPOUND | pKa |
|---|---|
| $\text{H}_4\text{Ru}_4(\text{CO})_{12}$ | 11.7 |
| $\text{H}_4\text{FeRu}_3(\text{CO})_{12}$ | 13.4 |
| $\text{H}_2\text{Ru}_4(\text{CO})_{13}$ | 14.7 |
| $\text{H}_2\text{FeRu}_3(\text{CO})_{13}$ | 14.3 |
| $\text{H}_2\text{Os(CO)}_4$ | 12.8 |
| $\text{H}_4\text{Os}_4(\text{CO})_{12}$ | 12.0 |

There are several transition metal carbonyls that have been found to provide protonated carbonyl species that have acid dissociations outside the range of most protonated tertiary amines considered. For instance, dicobalt octacarbonyl $\text{Co}_2(\text{CO})_8$ forms on reaction with hydrogen the protonated species $\text{HCo(CO)}_4$ which dissociates as a strong acid and all of it reacts with the excess of tertiary amine in solution to form the protonated amines species and the cobalt tetracarbonyl anion. The absence of the protonated cobalt carbonyl species in the catalytic system prevents the occurance of a comparable system as described above in the case of the iron carbonyl system. On the otherhand, the conjugate bases, $\text{Re(CO)}_5^-$ and $\text{Ni(CO)}_3^{2-}$ formed from rhenium or nickel carbonyls are so basic as to capture carbon dioxide into solution as carbonate anions such as $\text{MeOCO}_2^-$. Such systems are so basic as to prevent or possibly hinder the present catalytic reactions without the removal of the carbonate produced.

The tertiary amine selected for the catalytic system can be one in which three separate groups are substituted on the amine nitrogen, such as trimethylamine. It also can be one in which the nitrogen appears in a heterocyclic ring or include double bonds in the substitution such as in 2-pyridinol. More than one amine group may appear in the compound such as in 1, 4-diazabicyclooctane. Most of the tertiary amines considered will have protonated species with pKa's in the range of 8 to 12 and accordingly match those of the selected protonated transition metal carbonyl.

Tertiary amines are selected over secondary and primary amines to prevent or minimize formation of insertion products such as formamides, nitrogen-substituted formamides and nitrogen substituted ureas.

The preferred tertiary amines include acyclic, alicyclic and heterocyclic amines such as trimethylamine, N-methylpyrroldine, 1, 4-diazabicyclooctane, dimethylneopentylamine, 2-pyridinol, 1,8-bis(dimethylamino)-naphthalene and mixtures of these amines. The tertiary amines should be of sufficiently low volatility to permit them to remain in the reactor solution as overhead gas including product and excess reaction gases are removed. In the contemplated temperature range of 180°-220° C. and 100-400 atmospheres, there are many tertiary amines including those suggested above that can be employed. However, trimethylamine is somewhat more volatile than desired.

The tertiary amines selected preferably include only saturated groups to avoid reaction with other constituents of the catalytic system. However, certain ring compounds such as 2-pyridinol may be sufficiently stable in this regard. Certain benzyl amines tend to permit transfer of methyl groups from the amine nitrogen to form lower order amines and accordingly are not preferred.

It is preferable to provide amines whose substituted groups do not have beta hydrogen atoms. Such beta hydrogen as in triethylamine tend to be lost in Hofman degradations with the formation of olefins. One amine that may be particularly well suited from the standpoint of low volatility and absence of beta hydrogen is dimethylneopentylamine. Since the beta carbon atom on the neopentyl substituent is connected only to carbons, no beta hydrogen exists to urge degradation to olefin. Consequently, the added molecular weight and lower volatility of this compound can be obtained without increased risk of amine degradation.

Although the above tertiary amines have been described as preferred for use in the catalytic system of this development, it will be understood that various other amines such as triethylamine, tripropylamine and others that may undergo various degrees of degradation or in some other manner be less desirable can also be employed in accordance with the present invention, but with somewhat less advantageous results.

The co-solvent selected for use with methanol in the catalytic system and method of the present development is one that is generally unreactive with the constituents of the solution. Methanol can be selected as the sole solvent or used with the co-solvent. Co-solvents with higher boiling point than methanol or ethanol are preferred to provide a stable catalytic liquid solution as reaction vapor is withdrawn. The high boiling co-solvent selected is one which in solution with ethanol and methanol provides a vapor phase with a higher concentration of ethanol and methanol than their respective concentrations in solution to permit a vapor-liquid type separation. Suitable co-solvents contemplated are dimethyl ether of diethylene glycol (diglyme), ethoxymethanol, tetraglyme, butanol, other higher alcohols or glycols, decalin and mixtures of these various solvents.

One manner of performing the method of the present invention is now described by reference to the Figure. A reactor 11 contains the homogeneous liquid catalytic system 13 as described in detail above. Anhydrous methanol or methanol with no more than 4% water enters at line 15. A gas mixture of carbon monoxide and hydrogen enters the reactor in line 17. Such gas mixtures can be conveniently provided from the gas product of a coal or other carbonaceous material gasification process in which the carbon monoxide is typically present in about 2 to 3 times that of the hydrogen partial pressure. This provides a slight excess in the 2:1 stoichiometric carbon monoxide to hydrogen requirement of the overall reaction of the present invention.

The methanol provided in line 15 may be provided from a number of commercially known sources and processes. For instance, methanol can be produced by disstillation of the fermentation product of wood or other biomass. It is also available in the catalytic hydrogenation of carbon monoxide, for instance, by passing the hydrogen enriched products of a coal gasifier over a suitable metal oxide e.g. copper-zinc chromite catalysts. Should methanol be prepared from this gasifier product, excess monoxide and hydrogen that remain unreacted may be passed directly upon compression into reactor 11 of the present process. Since methanol is converted to methyl formate by its reaction with carbon monoxide in the reaction series resulting in ethanol, methyl formate may be provided with or in place of the methanol. For instance the initial reactor charge may be provided with methyl formate.

The catalytic reaction in the iron carbonyl—tertiary amine process is preferably carried out at a temperature of 180°-220° C., pressures of 100-400 atmospheres and with a measured pH in the homogeneous catalytic solution of 9—13. It is preferred that the carbon monoxide partial pressure be at least about 75 atmospheres to minimize formation of $FeCO_3$ precipitates in the reaction solution.

The ethanol produced in the reactor can be removed for further separation by withdrawing vapor through line 19 or by withdrawing liquid through line 21. It is preferred that this withdrawal be made from the vapor phase to eliminate or reduce the need to separate and recycle catalyst and high boiling solvent to the reactor. The vapor flow passes through a condenser 23 with the noncondensable gases including the carbon dioxide produced passed through line 24 to an acid gas separation unit 25 such as a scrubber or an adsorpsion unit where the carbon dioxide can be removed at 27. The remaining gases such as unreacted carbon monoxide and hydrogen as well as by-products, for instance methane, can be withdrawn in line 29 for use or recycle into the reactor. If the gas stream includes substantial amounts of methane, it can be steam reformed to hydrogen and carbon monoxide and dried prior to recycle to reactor 11. Alternatively, this gas flow may be suitable as a fuel for other process requirements.

The condensate 31 from condenser 23 may be recycled into the reactor through line 35 or fed into a fractionation column 33 through line 37 depending on its composition. For instance, if the condensate includes large amounts of ethanol it can be fed to the fractionation column 33. However, if it is primarily methanol, it can be returned to reactor 11 through line 35. It may be desirable to split the flow of condensate with portions to both to the reactor and to the fractionation column.

The liquid stream withdrawn through line 21 can be fed into fractionation column 33 at a lower level than the feed point of the condensed vapors at 37. The withdrawal through line 21 may or may not be necessary depending on whether a sufficient flow of ethanol can be withdrawn with the vapor stream through line 19.

Fractionation column 33 is used to separate the ethanol product from methanol and from the less volatile solvents and catalysts. The methanol is withdrawn from the top of the column at 41 and the less volatile materials are withdrawn from the bottom at line 43. The high boiling materials at 43 can include the transition metal carbonyl, tertiary amine and high boiling solvents that are less volatile than ethanol. This stream at 43 will ordinarily be recycled to the reactor 11 with any needed make up or upgrading of solvent or catalyst. The reflux condensor 45 is illustrated at the top of fractionated column 33 for providing a liquid reflux 47 and the recycled stream 41 for returning methanol to reactor 11.

Although the present process is described above in terms of a continuous reactor and fractionation unit to separate the ethanol product, it will be clear that various other unit operations and process steps well known in the art can also be employed. For example, the reaction may be performed in batch reactors with liquid products subsequently removed for separation in batches or with a plurality of batch reactors alternately feeding the continuously operating separation column. A separate reactor can be provided to convert methanol at least partly to methyl formate. It also may be advantageous to employ a series of reactors to incrementally increase the ethanol concentration within the liquid and/or gas phases prior to the final fractionation separation. As discussed above, the feed to the fractionation column may be from either or both the gas or liquid phases from the reactor and various streams within and from the process may either be recycled into the reactor or employed for beneficial purposes as will be apparent to one skilled in the art.

The following examples are presented merely to illustrate but not to limit the scope of the present invention.

EXAMPLE I (M-32)

About 180 cc of solution containing 3.4 M $NMe_3$, 0.17 M $Fe(CO)_5$ (4 cc) and the remainder (120 cc) methanol was placed in a stirred autoclave from which air had been purged. The solution was reacted with $CO/H_2$ gas at a partial pressure ratio of 3/1 respectively, at 200° C. and a total pressure of 375 atmospheres. Samples taken after 7.7 and 19.8 hours showed 0.7 M and 2.7 M EtOH, respectively, the latter value corresponding to 20% conversion of MeOH to EtOH.

EXAMPLE II (M-34)

Addition of Methyl Formate

Since methyl formate is formed in the equilibrium of equation 1 above, it is added to the initial charge of the autoclave at about 3 M concentration to 12.6 M MeOH. The reaction was carried out as in Example I but with 300 atmospheres total $CO/H_2$ pressure. After 6 hours the liquid contained 1.31 M ethanol corresponding to 8.4% conversion of methanol and methyl formate.

EXAMPLE III (M-35)

Addition of Water

The solution of Example II was altered by the addition of 14 cc of water (4.4 M). After 6 hours of stirred exposure to $CO/H_2$ gases as in the previous Examples less than 0.1 g ethanol was formed in the liquid for a percent conversion of only 0.1%. It is believed that the water gas shift reaction: $H_2O+CO \rightarrow H_2+CO_2$ is catalyzed by the iron carbonyl in solution to the detriment of ethanol production when water is present.

EXAMPLE IV (M-44)

Addition of Ethanol

The approximate conditions of Example I were carried out with the addition of 70 cc (7.2 M) EtOH to 50 cc (7.4 M) MeOH to see if the presence of product will terminate the reaction. After about 6 hours of reaction, EtOH was present in the liquid at 7.6 M to 5.0 M MeOH and CO was still being consumed. Ethyl formate was detected at about 0.4 M but, no higher alcohols were detected.

EXAMPLE V (M-38)

Less Volatile Co-Solvent

A reaction mixture similar to that in Example II but including 65 cc of dimethylether of diethylene glycol (diglyme), 18 cc MeOH and 36 cc of methyl formate as solvent. After only 2 hours reaction the solution contained 4.8 cc of EtoH for a conversion of 9.2% based on methanol and methyl formate.

EXAMPLE VI (M-42)

Increased Transition Metal Carbonyl Concentration

The initial reaction mixture of Example II was altered by increasing the $Fe(CO)_5$ concentration from 0.17 M to 0.81 M. After 4½ hours reaction 23.8% of the MeOH and methyl formate were converted to EtOH.

EXAMPLE VII (M-43)

Increased Temperature

The reaction mixture of Example II was maintained at 220° C. for 2 hours to provide a conversion of 13% MeOH and methyl formate to EtOH.

EXAMPLE VIII (M-41)

Less Volatile Tertiary Amine

The reaction mixture of Example II is changed by substituting 3.3 M N-Methylpyrrolidine for the more volatile trimethylamine. After 6 hours of reaction at the Example II conditions 7.4% conversion to EtOH was obtained. Some decomposition by Hoffmann degradation, ultimately to trimethylamine, was noted.

Tables II and III below give additional data respecting the above Examples.

TABLE II

LIQUID SOLUTIONS
INITIAL SOLUTION
GRAM MOLES PER LITER

|         | Fe(CO)$_5$ | MeOH | HCO$_2$Me | NR$_3$[a] | Co-Solvent |
|---------|-----------|------|-----------|-----------|------------|
| EX I    | 0.17      |      | 0         | 3.4       | 0          |
| EX II   | 0.17      | 12.6 | 3.0       | 3.3       | 0          |
| EX III  | 0.17      | 11.6 | 2.8       | 3.0       | 4.4 (H$_2$O) |
| EX IV   | 0.17      | 7.3  | 0         | 3.3       | 7.0 (EtOH) |
| EX V    | 0.17      | 2.5  | 3.3       | 3.3       | 2.7 (Diglyme) |
| EX VI   | 0.81      | 11.7 | 3.0       | 3.0       | 0          |
| EX VII  | 0.17      | 12.5 | 3.3       | 3.3       | 0          |
| EX VIII | 0.17      | 10.7 | 3.3       | 0         | 0          |

SAMPLES - 6 HRS
GRAM MOLES PER LITER

|         | pH   | MeOH | HCO$_3$Me | EtOH         | NR$_3$[a] | HFe(CO)$_4$⁻    | % CONV        |
|---------|------|------|-----------|--------------|-----------|-----------------|---------------|
| EX I    |      |      |           | 0.7 (7.7h)   |           | 0.17            | 5.2 (7.7h)    |
| EX II   | 10.6 | 10.7 | 1.0       | 1.31         | 1.5       | 0.17            | 8.4           |
| EX III  | 9.6  | 11.0 | 0.67      | 0.02         | 0.3       | 0.17            | 0.1           |
| EX IV   | 10.8 | 5.0  | 0         | 7.6          | 1.3       | 0.14            |               |
| EX V    | 9.6  | 2.9  | 0.56      | 0.64         | 3.6       | 0               | 9.7           |
| EX VI   | 10.1 | 7.0  | 0.78      | 3.60         | 1.5       | 0.16 (4.5h)     | 23.8 (4.5h)   |
| EX VII  | 9.5  | 12.1 | 0.97      | 2.30         | 2.4       | 0.02 (3h)       | 16.8 (3.0h)   |
| Ex VIII | 11.0 | 8.6  | 0.63      | 1.07         | 0.4       | 0.19            | 7.4           |

[a] Trimethylamine except in EX VIII where N-Methylpyrrolidine was used.

TABLE III

ANALYSES OF NONCONDENSABLE HEAD GAS[a]
SAMPLES - 6 HRS

| | MOLE % | | | |
|---|---|---|---|---|
|         | H$_2$ | CO   | CH$_4$ | CO$_2$ |
| EX II   | 19.8  | 61.2 | 5.6    | 13.4   |
| EX III  | 36.1  | 43.5 | 1.0    | 19.3   |
| EX IV   | 25.5  | 52.6 | 8.2    | 13.8   |
| EX V    | 14.6  | 70.5 | 4.8    | 10.0   |
| EX VI[b] | 9.3  | 51.7 | 9.7    | 29.3   |
| EX VII  | 20    | 48   | 11.3   | 20.5   |
| EX VIII | 22.1  | 50.6 | 6.0    | 21.3   |

[a] A gas mixture of 3/1, CO/H$_2$ was used in the initial charge and in restoring the pressure drop.
[b] 3 h sample.

EXAMPLE IX

(M-52)

Continuous Gas Flow

A reaction mixture similar to that used in Example VI was filled into an autoclave fitted with a reflux condenser on a gas discharge from the vapor space. Suitable pressure regulators permitted CO/H$_2$ flow at about 3/1 ratio, 300 atmospheres and 500 STP cc/min. After 4 hours reaction at 200° C. a conversion of 20% to EtOH was obtained. The concentrations of CO$_2$ in the vapor space remained steady at about 8% and the HFe(CO)$_4$⁻ reactive species remained at 60% of the original charge. This is compared to 29% CO$_2$ in the head space and only 20% original HFe(CO)$_4$⁻ remaining in the Example VI run.

EXAMPLE X

An autoclave charged with 160 ml (17.6 M) MeOH, 3.17 M NMe$_3$, and 3.41 g Ru$_3$(CO)$_{12}$ was reacted with about 300 atmospheres 3/1, CO/H$_2$ gas at 200° C. Only a portion of the Ru$_3$(CO)$_{12}$ dissolved. After 3½ hours, 0.164 M EtOH and 0.961 M methyl formate was present in the liquid. Temperature was later raised to 235° C. which resulted in slightly more than doubling the rate of EtOH production per mole of ruthenium.

It will be clear from the above that a catalytic system and method is provided for the production of ethanol with minimal water and other liquid by-products. Ethanol is produced by the reaction of methanol or methyl formate with gases including carbon monoxide and hydrogen at partial pressures typical of those present in a gasifier product prior to enriching the hydrogen content. As is known, the methanol and methyl formate also can be prepared from carbon monoxide and hydrogen gas. This process through use of a novel catalyst combination of selected transition metal carbonyls and selected tertiary amines with comparable acid dissociation in protonated species permits excellent selectivity of ethanol over other aliphatic compounds. Compounds such as ethers acetates, aldehydes and higher alcohols as well as water have been produced in previous homogeneous catalytic processes.

It will also be clear that even though the present method and system are described in terms of specific embodiments, that various changes in the materials, process steps and techniques can be made by those skilled in the art within the scope of the claims.

The embodiment of the invention in which an exclusive property or privilege is claimed are defined as follows:

1. A method of selectively producing ethanol from methanol comprising:
    forming an organic solution including methanol solvent and further including in solution a tertiary amine and, a transition metal carbonyl selected from the group consisting of iron carbonyls, ruthenium carbonyls and combinations thereof;
    contacting the organic solution with a flow of gas containing H$_2$ and CO to react with methanol and form ethanol and CO$_2$ substantially without the production of water in accordance with the overall reaction;

$$MeOH + 2CO + H_2 \rightarrow EtOH + CO_2$$

recovering ethanol as product.

2. The method of claim 1 wherein the reaction occurs at a temperature of 180° to 220° C. and a pressure of 100 to 400 atmospheres.

3. The method of claim 1 wherein the gas has a greater partial pressure of CO than that of $H_2$.

4. The method of claim 3 wherein the gas has about three to one, CO to $H_2$ partial pressure ratio.

5. The method of claim 3 wherein the gas has a CO partial pressure of at least 75 atmospheres.

6. The method of claim 1 wherein the solution contains less than 4 weight percent water.

7. The method of claim 1 wherein ethanol is recovered by disstilation.

8. The method of claim 1 wherein a flow of gas containing ethanol, methanol, carbon dioxide, hydrogen and carbon monoxide are withdrawn from above said solution, partially condensed to remove methanol and ethanol liquid, and the ethanol is separated from the condensed liquid by fractionation.

9. The method of claim 8 wherein the gas remaining after partial condensation is treated to remove carbon dioxide and returned to said liquid mixture for further reaction.

10. The method of claim 1 wherein the transition metal carbonyls are carbonyls of Fe.

11. The method of claim 1 wherein said transition metal carbonyls species in solution are provided by blending into solution a transition metal carbonyl selected from the group consisting of $Fe(CO)_5$, $Ru_3(CO)_{12}$ and mixtures thereof.

12. The method of claim 1 wherein the transition metal carbonyls in solution include $HFe(CO)_4^-$ 13. The method of claim 1 wherein said transition metal carbonyl and tertiary amine each have protonated species in said solution in quantities in excess of $10^{-5}$ moles per liter.

14. The method of claim 1 wherein said tertiary amine is selected from the group consisting of acyclic amines, alicyclic amines and heterocyclic amines.

15. The method of claim 14 wherein the tertiary amine species are saturated compounds.

16. The method of claim 14 wherein the tertiary amine is selected from the group of amines consisting of trimethylamine, N-methylpyrrolidine, 1-4 diazabicyclooctane, dimethylneopentylamine, 2-pyridinol, 1,8-bis(dimethylamino)naphthalene and mixtures thereof.

17. The method of claim 1 wherein the solution includes the combination of the species, $HFe(CO)_4^-$, a tertiary amine, $Fe(CO)_4^{-2}$ and a protonated cation of the tertiary amine.

18. The method of claim 1 wherein methyl formate is included in the solution.

19. The method of claim 1 wherein said solution has a measured pH of 9 to 13.

20. The method of claim 1 wherein the organic solvent includes in combination with methanol an organic liquid that is less volatile than ethanol to provide a vapor phase over the solution with a higher concentration of ethanol and of methanol than their respective concentrations in solution.

21. The method of claim 20 wherein the organic liquid is selected from the group of solvents consisting of diglyme, tetraglyme, ethoxyethanol, saturated alcohols of four or more carbons, glycols and mixtures thereof.

* * * * *